United States Patent [19]

Demosthene et al.

[11] 4,226,995
[45] Oct. 7, 1980

[54] PREPARATION PROCESS OF 2-CHLORO PYRIMIDINE

[75] Inventors: Claude G. Demosthene, Aramon; Christian R. Aspisi, Boulbon, both of France

[73] Assignee: "Societe Anonyme" Expansia, Paris, France

[21] Appl. No.: 38,177

[22] Filed: May 11, 1979

[30] Foreign Application Priority Data

May 31, 1978 [GB] United Kingdom ............... 25655/78

[51] Int. Cl.³ .......................................... C07D 239/30
[52] U.S. Cl. .................................................... 544/334
[58] Field of Search ......................................... 544/334

[56] References Cited

U.S. PATENT DOCUMENTS 2,477,409  7/1969  Howard ................................. 544/334
3,711,480  1/1973  Ruetman ............................... 544/334

Primary Examiner—Nicholas S. Rizzo
Attorney, Agent, or Firm—Eyre, Mann, Lucas & Just

[57] ABSTRACT

Preparation process of 2-chloro pyrimidine from 2-amino pyrimidine, hydrochloric acid and an alkali metal nitrite, the reagents being in substantially similar proportions as in the previously known methods, consisting in preparing a mixture of hydrochloric acid and of a non polar solvent of low boiling point, then adding 2-amino pyrimidine wherein there is slowly added, at room temperature, the chloride of a metal selected from the group consisting of the transition metals, tin, antimony, thallium and zinc, then introduced, under an inert gas circulation, the selected nitrite at a temperature not exceeding 10° C. and finally poured the reaction mixture in iced water.

3 Claims, No Drawings

PREPARATION PROCESS OF 2-CHLORO PYRIMIDINE

The present invention relates to an improved process for the preparation of 2-chloro pyrimidine.

This compound is already known but, so far, the processes used for its preparation are not very satisfactory, more particularly with respect to the yield. One of these synthesis is described in "Organic Syntheses," volume IV page 182; according to this method, the reaction is performed between −15° C. and −10° C. (use of a diazonium salt in the presence of hydrochloric acid); the yield is always lower than 30%. A slight improvement of this process has been later described by KRCHNAK U. et ARNOLD Z., Czechoslow. Chem. Commun. 40, 1390 (1975), with the use of a 5 M lithium chloride; nevertheless, the yield was lower than 50%. It has been noticed that if it was possible to increase the concentration in chloride ions, the yield might be significantly improved. After extensive investigations, it has been found that the suitable chlorides for this purpose were those of the transition metals and of tin, antimony, thallium and zinc. The most favourable reaction conditions have been encountered by using zinc chloride, instead of the previously used lithium chloride, which rendered possible the reaction at a higher temperature than previously, with a correlative increase in the yield. Zinc chloride leads to an intermediate complex of better stability; it also presents a good solubility in the reacting mixture, is easy to recover and comparatively cheaper to use.

As to the solvents to be used, any non polar solvent with a low boiling point is suitable; very good results are obtained with methylene chloride.

More precisely, this invention relates to an improved preparation process of 2-chloro pyrimidine from 2-amino pyrimidine, hydrochloric acid and an alkali metal nitrite, the reagents being in substantially similar proportions as in the previously known methods, consisting in preparing a mixture of hydrochloric acid and of a non polar solvent of low boiling point, then adding 2-amino pyrimidine in which there is slowly added, at room temperature, the chloride of a metal selected from the group consisting of the transition metals, tin, antimony, thallium and zinc, then introduced, under an inert gas circulation, the selected nitrite at a temperature not exceeding 10° C. and finally poured the reaction mixture in iced water.

According to a preferred feature of the invention, the metal chloride is zinc chloride.

According to another preferred feature of the invention, the non polar solvent is methylene chloride.

The invention will be better understood from the description of the following example:

EXAMPLE

In a 250-liter reactor is prepared the mixture of 27 kg (approximately 265 mols) of concentrated hydrochloric acid (d=1.18) and 35 kg -or 28 liters- of methylene chloride. There are thus added, under stirring, 8 kg (84.12 mols) of 2-amino pyrimidine which leads to a solution. After cooling, it is added between 15° and 20° C., 33 kg (242.5 mols) of zinc chloride; the addition is effected in about 30 minutes and leads to a mustard-coloured suspension.

After a further cooling to 5° or 10° C. and an introduction of a nitrogen flow, there are added (in three hours and a quarter) 10 kilos (i.e. 145 mols) of sodium nitrite. There is an emission of nitrous vapours; 30 minutes after the end of this introduction, the reacting mixture is poured in 150-liters of iced water and allowed to rest.

The organic phase is then separated and the aqueous phase is treated 4 times by 50 kg (40 liters) of methylene chloride. All the washing organic phases are gathered and dried on 3 kg of dry sodium sulphate, then filtered, concentrated at ordinary pressure at 45°–50° C.; this allows the recovery of about 80% of the methylene chloride.

The remaining organic phase is then concentrated in a rotative evaporator under reduced pressure (25 mm of Hg) at a temperature not exceeding 35° C., then dried for one and a half hour at 40° C.

There are obtained 6.6 kg (yield 69%) of 2-chloro pyrimidine which is a yellowish crystalline powder melting at 63°–65° C. (Koffler), the analysis of which shows a perfect correspondence with the formula:

$C_4H_3N_2Cl$.

We claim:

1. Preparation process of 2-chloro pyrimidine from 2-amino pyrimidine, hydrochloric acid and an alkali metal nitrite, the reagents being in substantially similar proportions as in the previously known methods, consisting in preparing a mixture of hydrochloric acid and of a non polar solvent of low boiling point, then adding 2-amino pyrimidine characterized in that, there is slowly added, at room temperature, the chloride of a metal selected from the group consisting of the transition metals, tin, antimony, thallium and zinc, then introduced, under an inert gas circulation, the selected nitrite at a temperature not exceeding 10° C. and finally poured the reaction mixture in iced water.

2. Preparation process according to claim 1 wherein metal chloride is zinc chloride.

3. Preparation process according to claim 1 or 2 wherein non polar solvent is methylene chloride.

* * * * *